(12) United States Patent
Wang et al.

(10) Patent No.: US 11,857,813 B2
(45) Date of Patent: Jan. 2, 2024

(54) HIGH INTENSITY FOCUSED ULTRASOUND SYSTEMS FOR TREATING TISSUE

(71) Applicant: University of Washington, Seattle, WA (US)

(72) Inventors: Yak-Nam Wang, Seattle, WA (US); Michael R. Bailey, Seattle, WA (US); Tatiana D. Khokhlova, Seattle, WA (US); Wayne Kreider, Seattle, WA (US); Adam D. Maxwell, Seattle, WA (US); George R. Schade, Seattle, WA (US); Vera A. Khokhlova, Seattle, WA (US)

(73) Assignee: University of Washington, Seattle, WA (US)

( * ) Notice: Subject to any disclaimer, the term of this patent is extended or adjusted under 35 U.S.C. 154(b) by 495 days.

(21) Appl. No.: 16/927,860

(22) Filed: Jul. 13, 2020

(65) Prior Publication Data

US 2021/0038924 A1 Feb. 11, 2021

Related U.S. Application Data

(63) Continuation of application No. 15/126,131, filed as application No. PCT/US2015/023306 on Mar. 30, 2015, now abandoned.
(Continued)

(51) Int. Cl.
*A61N 7/00* (2006.01)
*A61N 7/02* (2006.01)

(52) U.S. Cl.
CPC ........ *A61N 7/02* (2013.01); *A61N 2007/0004* (2013.01); *A61N 2007/0091* (2013.01)

(58) Field of Classification Search
None
See application file for complete search history.

(56) References Cited

U.S. PATENT DOCUMENTS

| 6,589,173 B1 | 7/2003 | Mitragotri |
| 6,824,516 B2 | 11/2004 | Batten et al. |

(Continued)

FOREIGN PATENT DOCUMENTS

| CN | 103025890 A | 4/2013 |
| WO | 2009094554 A2 | 7/2009 |

(Continued)

OTHER PUBLICATIONS

AACR. Liquid Biopsy Workshop Session II transcript.
(Continued)

*Primary Examiner* — Patricia J Park
(74) *Attorney, Agent, or Firm* — Lee & Hayes, P.C.

(57) ABSTRACT

High intensity focused ultrasound systems for treating tissue are disclosed herein. A system of treating tissue in a patient in accordance with an embodiment of the present technology can include, for example, an ultrasound source having a focal region and configured to deliver high intensity focused ultrasound energy to a target site in tissue of the patient. The system can further include a controller operably coupled to the ultrasound source. The controller comprises a pulsing protocol for delivering the high intensity focused ultrasound energy with the ultrasound source to the target site. The controller is configured to cause the ultrasound source to pulse high intensity focused ultrasound waves to lyse cells in a volume of the tissue of the subject while preserving an extracellular matrix in the volume of the tissue exposed to the high intensity focused ultrasound waves.

18 Claims, 5 Drawing Sheets

Related U.S. Application Data

(60) Provisional application No. 62/072,947, filed on Oct. 30, 2014, provisional application No. 61/973,032, filed on Mar. 31, 2014.

(56) References Cited

U.S. PATENT DOCUMENTS

| | | | |
|---|---|---|---|
| 8,278,053 | B2 | 10/2012 | Glazer et al. |
| 2005/0043726 | A1 | 2/2005 | McHale et al. |
| 2007/0244568 | A1* | 10/2007 | Matsuda ............ A61L 27/3683 623/23.72 |
| 2008/0183200 | A1 | 7/2008 | Babaev et al. |
| 2008/0319356 | A1 | 12/2008 | Cain et al. |
| 2009/0036774 | A1* | 2/2009 | Weng ................ A61N 7/00 601/2 |
| 2009/0269317 | A1 | 10/2009 | Davalos et al. |
| 2010/0009400 | A1 | 1/2010 | Glazer et al. |
| 2010/0092424 | A1 | 4/2010 | Sanghvi et al. |
| 2010/0241005 | A1 | 9/2010 | Darlington et al. |
| 2010/0261176 | A1 | 10/2010 | Mitragotri et al. |
| 2011/0059053 | A1* | 3/2011 | Chauhan ............. C12N 15/87 435/41 |
| 2011/0251528 | A1* | 10/2011 | Canney ............ A61N 7/02 601/3 |
| 2012/0010541 | A1 | 1/2012 | Cain et al. |
| 2012/0259250 | A1 | 10/2012 | Sapozhnikov et al. |
| 2013/0018260 | A1 | 1/2013 | Sanghvi et al. |
| 2013/0041293 | A1 | 2/2013 | Cain et al. |
| 2013/0066240 | A1 | 3/2013 | Van Heesch et al. |
| 2013/0171653 | A1 | 7/2013 | Doll et al. |
| 2013/0237780 | A1 | 9/2013 | Beasley et al. |
| 2014/0350677 | A1* | 11/2014 | Chang ............... A61K 27/3691 424/548 |
| 2015/0153909 | A1 | 6/2015 | Zubas et al. |
| 2017/0071515 | A1 | 3/2017 | Chevillet et al. |
| 2017/0072228 | A1 | 3/2017 | Wang et al. |

FOREIGN PATENT DOCUMENTS

| | | |
|---|---|---|
| WO | 2012162133 A1 | 11/2012 |
| WO | 2015153441 A1 | 10/2015 |
| WO | 20150153909 A2 | 10/2015 |

OTHER PUBLICATIONS

Albertsen, PC , "PSA testing: public policy or private penchant?", (Translated from eng) Jama 296(19):2371-2373, 2006.
Arroyo, JD et al., "Argonaute2 complexes carry a population of circulating microRNAs independent of vesicles in human plasma", Proc Natl Acad Sci U S A 108(12):5003-5008 (in eng), 2011.
Aus, G. , "Current status of HIFU and cryotherapy in prostate cancer—a review", (Translated from eng) Eur Urol 50(5):927-934; discussion 934, 2006.
Baldwin, K. , "Liquid Biopsy May Help Guide Treatment Decisions for Advanced Solid Tumors", ASCO Press Release. Jun. 4, 2016.
Baughman, D. et al., "Exosome Diagnostics Launches World's First Exosomal RNA-Based Liquid", Biopsy, ExoDx™ Lung(ALK). Jan. 21, 2016. http://www.exosomedx.com/news-events/press-releases/exosome-diagnostics-launches-worlds-first-exosomal-rna-based-liquid-biopsy.
Belcher, K. , "Therapy Monitoring Emerges as a Promising Application for Liquid Biopsy", Frost & Sullivan Press Release, Jan. 15, 2016., Accessed at http://ww2.frost.com/news/press-releases/majority-users-identify-therapy-monitoring-promising-liquid-biopsy-application/.
Bettegowda, C. et al., "Detection of Circulating Tumor DNA in Early- and Late-Stage Human Malignancies. Science Translational Medicine", Feb. 19, 2014:vol. 6, Issue 224, pp. 224ra24 DOI: 10.1126/scitranslmed.3007094.
Blount, LV et al., "Point mutations in the Ki-ras2 gene of codon 12 in the Dunning R-3327 Prostatic Adenocarcinoma system", (Translated from eng) Prostate 28(1):44-50, 1996.
Borboroglu, PG et al., "Extensive repeat transrectal ultrasound guided prostate biopsy in patients with previous benign sextant biopsies", (Translated from eng) J Urol 163(1):158-162, 2000.
Calin, GA et al., "A MicroRNA signature associated with prognosis and progression in chronic lymphocytic leukemia", (Translated from eng) N Engl J Med 353(17):1793-1801, 2005.
Canney, M.S. et al., "Tissue erosion using shock wave heating and millisecond boiling in HIFU fields.", AIP Conf. Proc. 2010, 1215, 36-39.
Canney, MS et al., "Shock-induced heating and millisecond boiling in gels and tissue due to high intensity focused ultrasound.", Utrasound Med. Biol. Feb. 2010; 36(2):250-67.
Childberg, M. , "Liquid Biopsy: What's in a Name?", Marty Chilberg's Instablog. May 17, 2015. Accessed at http://seekingalpha.com/instablog/400846-marty-chilberg/4008696-liquid-biopsy-whats-in-a-name.
Desmond-Hellmann, S. et al., "Toward precision medicine: a new social contract?", (Translated from eng) Sci Transl Med 4(129):129ed123, 2012.
Diehl, F. et al., "Circulating mutant DNA to assess tumor dynamics", (Translated from eng) Nat Med 14(9):985-990, 2008.
Diehl, F. et al., "Detection and quantification of mutations in the plasma of patients with colorectal tumors", (Translated from eng) Proc Natl Acad Sci U S A 102(45):16368-16373, 2005.
Djavan, B. et al., "Safety and morbidity of first and repeat transrectal ultrasound guided prostate needle biopsies: results of a prospective European prostate cancer detection study", (Translated from eng) J Urol 166(3):856-860, 2001.
Dubinsky, TJ et al., "High-intensity focused ultrasound: current potential and oncologic applications", (Translated from eng) AJR Am J Roentgenol 190(1):191-199, 2008.
Esquela-Kerscher, A. et al., "Oncomirs—microRNAs with a role in cancer", (Translated from eng) Nat Rev Cancer 6(4):259-269, 2006.
FDA Press Release. FDA approves first blood test to detect gene mutation associated with non-small cell lung cancer. Jun. 1, 2016. http://www.fda.gov/NewsEvents/Newsroom/PressAnnouncements/ucm504488.htm.
Final Office Action dated Apr. 10, 2019 in U.S. Appl. No. 15/122,394 for Chevillet et al., filed Aug. 29, 2016, 40 pages.
Final Office Action dated Apr. 22, 2020 in U.S. Appl. No. 15/122,394 for Chevillet et al., filed Aug. 29, 2016, 40 pages.
Final Office Action dated Feb. 12, 2020 in U.S. Appl. No. 15/126,131 for Wang et al., filed Sep. 14, 2016, 26 pages.
Final Office Action dated Mar. 4, 2019 in U.S. Appl. No. 15/126,131 for Wang et al., filed Sep. 14, 2016, 30 pages.
Gerlinger, M. , "Intratumor heterogeneity and branched evolution revealed by multiregion sequencing", N Engl J Med. Mar. 8, 2012;366(10):883-92. doi: 10.1056/NEJMoa1113205. http://www.ncbi.nlm.nih.gov/pubmed/22397650.
Guardant Health press release. "Guardant Health Secures Series D Financing to Expand the Reach of its Digital Sequencing™ Platform in Oncology." Jan. 7, 2016., http://www.prnewswire.com/news-releases/guardant-health-secures-series-d-financing-toexpand-the-reach-of-its-digital-sequencing-platform-in-oncology-300200834.html.
Healthcare Bluebook accessed at http://www.healthcarebluebook.com.
HHHS. Principles for Codevelopment of an In Vitro Companion Diagnostic Device with a Therapeutic Product. Jul. 15, 2016., Document 1400027 http://www.fda.gov/ucm/groups/fdagov-public/@fdagov-meddev-gen/documents/document/ucm510824.pdf.
Hindson, BJ et al., "High-throughput droplet digital PCR system for absolute quantitation of DNA copy number", (Translated from eng) Anal Chem 83(22):8604-8610, 2011.
Hu, Z. et al., "Investigation of HIFU-induced anti-tumor immunity in a murine tumor model," Journal of Translational Medicine 5, Article No. 34 (2007). Jul. 11, 2007.
Hwang, JH et al., "Correlation between inertial cavitation dose and endothelial cell damage in vivo", Translated from eng) Ultrasound Med Biol, 32(10):1611-1619, 2006.
Hwang, JH et al., "Current status of clinical high-intensity focused ultrasound", (Translated from eng) Conf Proc IEEE Eng Med Biol Soc 2009:130-133, 2009.

(56) References Cited

OTHER PUBLICATIONS

Hwang, JH et al., "High-intensity focused US: a potential new treatment for GI bleeding", (Translated from eng) Gastrointest Endosc 58(1):111-115, 2003.

Hwang, JH et al., "Targeted venous occlusion using pulsed high-intensity focused ultrasound", (Translated from eng) IEEE Trans Biomed Eng 57(1):37-40, 2010.

Hwang, JH et al., "Vascular effects induced by combined 1-MHz ultrasound and microbubble contrast agent treatments in vivo", (Translated from eng) Ultrasound Med Biol 31(4):553-564, 2005.

International Search Report and Written Opinion dated Jan. 14, 2016, in International Application No. PCT/2015/024144, 16 pages.

International Search Report and Written Opinion dated Jul. 2, 2015, in International Application No. PCT/US2015/023306, 6 pages.

Isaacs, JT et al., "Genetic instability coupled to clonal selection as a mechanism for tumor progression in the Dunning R-3327 rat prostatic adenocarcinoma system", (Translated from eng) Cancer Res 42(6):2353-2371, 1982.

Isaacs, JT et al., "The characterization of a newly identified, highly metastatic variety of Dunning R 3327 rat prostatic adenocarcinoma system: the MAT LyLu tumor", (Translated from eng) Invest Urol 19(1):20-23, 1981.

Jung, K. et al., "Plasma matrix metalloproteinase 9 as biomarker of prostate cancer progression in Dunning (Copenhagen) rats", (Translated from eng) Prostate 54(3):206-211, 2003.

Kennedy, JE , "High-intensity focused ultrasound in the treatment of solid tumours", (Translated from eng) Nat Rev Cancer 5(4):321-327 , 2005.

Keshavarzi et al. "Treatment of Uterine Fibroid Tumors in an In Situ Rat Model Using High-Intensity Focused Ultrasound", Fertility and Sterility, vol. 80, (Sep. 2003), pp. 761-767.

Khokhlova, T. et al., "Simulated Release of Nucleic Acid Cancer Biomarkers by HIFU: A Study in a Rat Prostate Cancer Model", 13th International Symposium on Therapeutic Ultrasound, May 13, 2013, 78.

Khokhlova, TD et al., "HIFU for palliative treatment of pancreatic cancer", Journal of Gastrointestinal Oncology., Sep. 2011, 175-184.

Kroh, EM et al., "Analysis of circulating microRNA biomarkers in plasma and serum using quantitative reverse transcription-PCR", (Translated from eng) Methods 50(4):298-301, 2010.

Leary, RJ et al., "Development of personalized tumor biomarkers using massively parallel sequencing", (Translated from eng) Sci Transl Med 2(20):20ra14, 2010.

Leon, SA et al., "Free DNA in the serum of cancer patients and the effect of therapy", Cancer Res. Mar. 1977;37(3):646-50.

Li, M. et al., "BEAMing up for detection and quantification of rare sequence variants", (Translated from eng) Nat Methods 3(2):95-97, 2006.

Misale, S. et al., "Emergence of KRAS mutations and acquired resistance to anti-EGFR therapy in colorectal cancer", Nature 486, 532-536 (2012).

Mitchell, PS et al., "Circulating microRNAs as stable blood-based markers for cancer detection", Proc Natl Acad Sci U S A 105(30):10513-10518, 2008.

Mukherjee, S. , "The Cancer Biopsy of the Future Could be a Simple Blood Test", Fortune. Jun. 5, 2016. http://fortune.com/2016/06/05/asco-guardant-liquid-biopsy/.

NIH. Extracellular RNA Communication. May 19, 2016. http://commonfund.nih.gov/Exrna/index.

Non-Final Office Action dated Aug. 16, 2019 in U.S. Appl. No. 15/126,131 for Wang et al., filed Sep. 14, 2016, 24 pages.

Non-Final Office Action dated Nov. 20, 2018 in U.S. Appl. No. 15/126,131 for Wang et al., filed Sep. 14, 2016, 36 pages.

Non-Final Office Action dated Oct. 31, 2018 in U.S. Appl. No. 15/122,394 for Chevillet et al., filed Aug. 29, 2016, 41 pages.

Non-Final Office Action dated Sep. 19, 2019 in U.S. Appl. No. 15/122,394 for Chevillet et al., filed Aug. 29, 2016, 31 pages.

Ozkumur, E. et al., "Inertial Focusing for Tumor Antigen-Dependent and - Independent Sorting of Rare Circulating Tumor", Sci Transl Med . Apr. 3, 2013; 5(179): 179ra47. doi:10.1126/scitranslmed.3005616. http://www.ncbi.nlm.nih.gov/pubmed/23552373.

Pinheiro, LB et al., "Evaluation of a droplet digital polymerase chain reaction format for DNA copy number quantification", (Translated from eng) Anal Chem 84(2):1003-1011, 2012.

Rago, C. et al., "Serial assessment of human tumor burdens in mice by the analysis of circulating DNA", (Translated from eng) Cancer Res 67(19):9364-9370, 2007.

Ren, XL et al., "Extracorporeal ablation of uterine fibroids with high-intensity focused ultrasound: imaging and histopathologic evaluation", Translated from eng) J Ultrasound Med 26(2):201-212, 2007.

Roobol, MJ et al., "The value of different screening tests in predicting prostate biopsy outcome in screening for prostate cancer data from a multicenter study (ERSPC)", (Translated from eng) Prostate 67(4):439-446, 2007.

Roychowdhury, S. et al., "Advancing Precision Medicine for Prostate Cancer Through Genomics", (Translated from Eng) J Clin Oncol, 2013.

Roychowdhury, S. et al., "Personalized oncology through integrative high-throughput sequencing: a pilot study", (Translated from eng) Sci Transl Med 3(111):111ra121, 2011.

Saad, A. et al., "Acute periprostatic haematoma following a transrectal ultrasound-guided needle biopsy of the prostate", (Translated from eng) Prostate Cancer Prostatic Dis 5(1):63-64, 2002.

Sacher, A. et al., "Prospective Validation of Rapid Plasma Genotyping for the Detection of EGFR and KRAS Mutations in", JAMA Oncol. Published online Apr. 7, 2016. doi:10.1001/jamaoncol.2016.0173.

Sawyers, CL , "The cancer biomarker problem", (Translated from eng) Nature 452(7187):548-552, 2008.

Stefani, G. et al., "Small non-coding RNAs in animal development", (Translated from eng) Nat Rev Mol Cell Biol 9(3):219-230, 2008.

Stroun, M. et al., "The origin and mechanism of circulating DNA", (Translated from eng) Ann N Y Acad Sci 906:161-168, 2000.

Sullivan, L. et al., "Canadian experience with high intensity focused ultrasound for the treatment of BPH", (Translated from Eng) Can J Urol 6(3):799-805, 1999.

Sullivan, Laurie , "Liquid Biopsies for Cancer Screening: An Emerging Sector of the POC Blood Testing Market", BCC Research. Jun. 15, 2015 http://www.bccresearch.com/lifesciences/index/liquid-biopsies.

Terry, M. , "Illumina (ILMN) Raises $100 Million with Amazon (AMZN)'s Bezos, Bill Gates and Others to Launch Pan-Cancer Test", Jan. 11, 2016. http://www.biospace.com/News/illumina-raises-100-million-with-amazons-bezos/405100.

The Promise of Liquid Biopsy Technology. Utilizing Investigational Technologies in Oncology Trials. 2016 Novella Clinical.

Thompson, IM et al., "Finasteride improves the sensitivity of digital rectal examination for prostate cancer detection", (Translated from eng) J Urol 177(5):1749-1752, 2007.

Thompson, IM et al., "Prevalence of prostate cancer among men with a prostate-specific antigen level < or =4.0 ng per milliliter", (Translated from eng) N Engl J Med 350(22):2239-2246, 2004.

Tie, J. et al., "Circulating tumor DNA analysis detects minimal residual disease and predicts recurrence in patients with stage II", Science Translational Medicine Jul. 6, 2016: vol. 8, Issue 346, pp. 346ra92. DOI: 10.1126/scitranslmed.aaf6219.

Tu, J. et al., "Intravascular inertial cavitation activity detection and quantification in vivo with Optison", (Translated from eng) Ultrasound Med Biol 32(10):1601-1609, 2006.

Vlaisavljevich, E. et al., "Effects of tissue mechanical properties on susceptibility to histotripsy-induced tissue damage.", Phys. Med. Bio. Jan. 2014., 20;59(2):253-70.

Wake, N. et al., "Chromosomal changes associated with progression of the Dunning R-3327 rat prostatic adenocarcinoma system", (Translated from eng) Cancer Res 42(10):4131-4142, 1982.

Wang, YN et al., "Histological and biochemical analysis of mechanical and thermal bioeffects in boiling histotripsy lesions induced by high intensity focused ultrasound", (Translated from eng) Ultrasound Med Biol 39(3):424-438, 2013.

(56) References Cited

OTHER PUBLICATIONS

Winslow, R., "Genomic Health Plans Line of Liquid-Biopsy Tests for Cancer", Wall Street Journal. Jan. 11, 2015. http://www.wsj.com/articles/genomic-health-plans-line-of-liquid-biopsy-tests-for-cancer-1421023689.

Wolters, T. et al., "False-negative prostate needle biopsies: frequency, histopathologic features, and follow-up", (Translated from eng) Am J Surg Pathol 34(1):35-43, 2010.

Yuen, JS et al., "Clinical, biochemical and pathological features of initial and repeat transrectal ultrasonography prostate biopsy positive patients", (Translated from eng) Int J Urol 11(4):225-231, 2004.

Zhou, Y. et al., "Targeted long-term venous occlusion using pulsed high-intensity focused ultrasound combined with a pro-inflammatory agent", (Translated from eng) Ultrasound Med Biol 37(10):1653-1658, 2011.

Zill, O. et al., "Somatic genomic landscape of over 15,000 patients with advanced-stage cancer from clinical next-generation sequencing analysis of circulating tumor DNA", 2016 ASCO Annual Meeting. Abstract No. LBA11501. J Clin Oncol 34, 2016, http://meetinglibrary.asco.org/content/171265-176.

\* cited by examiner

HIGH INTENSITY FOCUSED ULTRASOUND SYSTEMS FOR TREATING TISSUE

CROSS-REFERENCE TO RELATED APPLICATION(S)

The present application is a continuation of U.S. patent application Ser. No. 15/126,131, titled "METHODS AND SYSTEMS FOR SELECTIVELY DISRUPTING TISSUE WITH HIGH INTENSITY FOCUSED ULTRASOUND," filed Sep. 14, 2016, which is a National Phase of International Patent Application No. PCT/US15/23306, titled "METHODS AND SYSTEMS FOR SELECTIVELY DISRUPTING TISSUE WITH HIGH INTENSITY FOCUSED ULTRASOUND," filed Mar. 30, 2015, which claims priority to U.S. Provisional Patent Application No. 61/973,032, titled "METHODS TO SELECTIVELY FRAGMENT AND REMOVE TISSUE WHILE SPARING EXTRACELLULAR MATRIX, VESSELS AND SIMILAR STRUCTURES," filed Mar. 31, 2014, and U.S. Provisional Patent Application No. 62/072,947, titled "METHODS TO SELECTIVELY FRAGMENT AND REMOVE TISSUE WHILE SPARING EXTRACELLULAR MATRIX, VESSELS AND SIMILAR STRUCTURES," filed Oct. 30, 2014, the disclosures of which are hereby incorporated by reference in their entireties.

STATEMENT REGARDING FEDERALLY SPONSORED RESEARCH OR DEVELOPMENT

This invention was made with government support under Grant Nos. 1 K01 EB015745-01 and 2 R01 EB007643-05 and T32 DK007779-11A1, awarded by the National Institutes of Health, and Grant No. SMST03402, awarded by the National Space Biomedical Research Institute. The government has certain rights in the invention.

TECHNICAL FIELD

The present technology relates generally to high intensity focused ultrasound systems for treating tissue.

BACKGROUND

Minimally invasive and non-invasive therapeutic ultrasound procedures can be used to ablate, necrotize, and/or otherwise damage tissue. High intensity focused ultrasound ("HIFU"), for example, has been used to thermally or mechanically damage tissue, such as tumors, cancerous tissue regions, and bleeding spots. HIFU thermal treatments increase the temperature of tissue at a focal region such that the tissue quickly forms a thermally coagulated treatment volume. HIFU treatments can also cause mechanical disruption of tissue with well-demarcated regions of mechanically emulsified treatment volumes. For certain medical applications, tissue emulsification may be more favorable than thermal damage because it produces liquefied volumes that are more easily removed or absorbed by the body than thermally coagulated solid volumes. However, the desired treatment region in the tissue may include vessels, stroma, and/or other structural components that may need to be preserved to allow the organ or other tissue structure containing the treatment region to continue to provide its intended function. Thus, there is a need to enhance HIFU procedures that mechanically disrupt tissue.

DETAILED DESCRIPTION

The present technology is directed toward systems and methods for selectively disrupting tissue with HIFU. In several embodiments, for example, an ultrasound source can pulse HIFU waves toward a volume of tissue that includes fibrous structures of an extracellular matrix ("ECM"). The pulsed HIFU waves can lyse cells in the tissue volume while allowing the ECM to remain at least substantially intact. In certain embodiments, the HIFU treatment can be used to decellularize a tissue mass to form a scaffold that can later be used for regenerative medicine and/or other applications.

The term "ECM" is used herein to describe the non-cellular fibrous and lattice structure of tissue composed of proteins, polysaccharides, and other molecules. For example, ECM can include the walls of blood and lymphatic vessels, dermis, fascia, neural sheaths, portal and binary structures in livers, the Bowman's capsule, glomerular membranes, ghosts of tubules, collecting ducts in kidneys, and other non-cellular tissue structures. Additionally, the term "target site" is used broadly throughout the disclosure to refer to any volume or region of tissue that may benefit from HIFU treatment.

Certain specific details are set forth in the following description and in FIGS. 1-5 to provide a thorough understanding of various embodiments of the technology. For example, several embodiments of HIFU treatments that destroy tissue are described in detail below. The present technology, however, may be used to destroy multi-cellular structures other than tissue. Other details describing well-known structures and systems often associated with ultrasound systems and associated devices have not been set forth in the following disclosure to avoid unnecessarily obscuring the description of the various embodiments of the technology. A person of ordinary skill in the art, therefore, will accordingly understand that the technology may have other embodiments with additional elements, or the technology may have other embodiments without several of the features shown and described below with reference to FIGS. 1-5.

Figure 1:
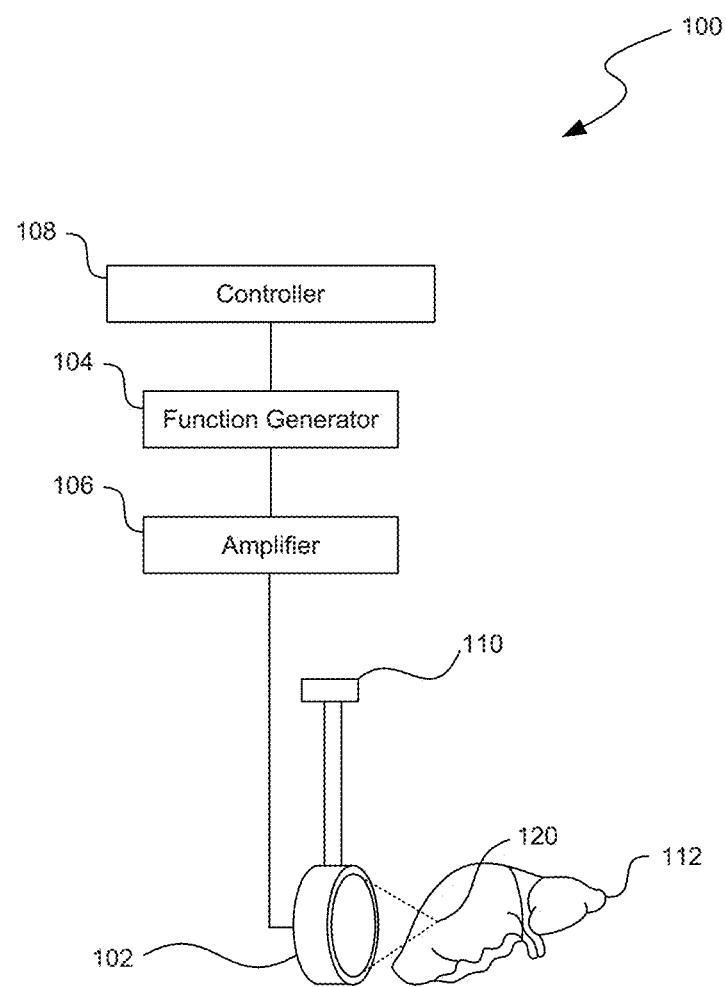
FIG. 1 is a partially schematic view of a HIFU system configured in accordance with an embodiment of the present technology.

FIG. 1 is a partially schematic view of a HIFU system 100 configured in accordance with an embodiment of the present technology. The HIFU system 100 can include an ultrasound source 102 operably coupled to a function generator 104 and, optionally, an amplifier 106. The ultrasound source 102 can be an ultrasound transducer that emits high levels of ultrasound energy toward a focus 120. The focus 120 can be a point, region, or volume at which the intensity from the ultrasound source 102 is the highest. For example, the ultrasound source 102 generally has a focal depth equal to the diameter of the ultrasound transducer. The function generator 104 (e.g., an Agilent 33250A function generator from Agilent of Palo Alto, CA) and the amplifier 106 (e.g., an ENI A-300 300 W RF amplifier from ENI of Rochester, NY) can drive the ultrasound source 102 to radiate HIFU waves and that induce boiling bubbles or cavitation proximate to the focus 120 to mechanically damage the tissue. Accordingly, the HIFU system 100 can implement a pulsing protocol in which ultrasound frequency, pulse repetition frequency, pulse length, duty cycle, pressure amplitude, shock wave amplitude, and/or other parameters associated with the HIFU emissions can be adjusted to generate HIFU waves to mechanically disrupt tissue. As described in further detail below, the HIFU system 100 can also selectively disrupt the tissue in the treatment volume to emulsify or lyse cells, while preserving the ECM for subsequent cell regrowth.

In various embodiments, the ultrasound source 102 can include a single-element device, a multi-element device, an extracorporeal device, an intracavitary device, and/or other devices or systems configured to emit HIFU energy toward a focus. For example, the ultrasound source 102 can be part of a Sonalleve MR-HIFU system made by Philips Healthcare of The Netherlands and/or a PZ 26 spherically focused piezoceramic crystal transducer made by Ferroperm Piezoceramics of Kvistgaard, Denmark. In certain embodiments, the ultrasound source 102 can have a frequency of approximately 0.5-20 MHz. For example, the ultrasound source 102 can have a frequency of about 1-3 MHz (e.g., 1.1 MHz, 1.2 MHz, 2 MHz, 2.1 MHz, etc.). In other embodiments, however, the frequency of the ultrasound source 102 can be higher than 20 MHz or lower than 0.5 MHz. In further embodiments, the source 102 can have different frequencies, aperture dimensions, and/or focal lengths to accommodate other therapeutic and diagnostic applications.

As shown in FIG. 1, the ultrasound source 102, the function generator 104, and/or other components of the HIFU system 100 can be coupled to a processor or controller 108 (shown schematically) that can be used to control the function and movement of various features of the HIFU system 100. In certain embodiments, the function generator 104 and the controller 108 can be integrated into a single device. The controller 108 can be a processing device, such as a central processing unit (CPU) or computer. The controller 108 can include or be part of a device that includes a hardware controller that interprets the signals received from input devices (e.g., the ultrasound source 102, the function generator 104, user input devices, etc.) and communicates the information to the features of the HIFU system 100 using a communication protocol.

The controller 108 may be a single processing unit or multiple processing units in a device or distributed across multiple devices. The controller 108 may communicate with the hardware controller for devices, such as for a display that displays graphics and/or text (e.g., LCD display screens—not shown). The controller 108 can also be in communication with a memory that includes one or more hardware devices for volatile and non-volatile storage, and may include both read-only and writable memory. For example, a memory may comprise random access memory (RAM), read-only memory (ROM), writable non-volatile memory, such as flash memory, hard drives, floppy disks, CDs, DVDs, magnetic storage devices, tape drives, device buffers, and so forth. A memory is not a propagating electrical signal divorced from underlying hardware, and is thus non-transitory. In certain embodiments, the controller 108 can also be coupled to a communication device capable of communicating wirelessly or wire-based with a network node. The communication device may communicate with another device or a server through a network using, for example, TCP/IP protocols.

The controller 108 can execute automated control algorithms to initiate, terminate, and/or adjust operation of one or more features of the HIFU system 100 and/or receive control instructions from a user. The controller 108 can further be configured to provide feedback to a user based on the data received from the HIFU system 100 via an evaluation/feedback algorithm. This information can be provided to the users via a display (e.g., a monitor on a computer, tablet computer, or smart phone; not shown) communicatively coupled to the controller.

In various embodiments, the HIFU system 100 can further include a positioning device 110 coupled to the ultrasound source 102 to aid in positioning the focus 120 of the ultrasound source 102 at a desired target site in the tissue. For example, the positioning device 110 can include a three-axis computer-controlled positioning system made by Velmex Inc. of Bloomfield, NY The positioning device 110 can also manipulate the ultrasound source 102 to move the focus 120 to different regions in the tissue to mechanically damage larger portions of the tissue 112. In other embodiments, the HIFU system 100 can include additional devices and/or some of the devices may be omitted from the HIFU system 100.

In operation, the ultrasound source 102 is positioned proximate to a volume of tissue 112 (e.g., an organ), and the focus 120 of the ultrasound source 102 is aligned with a target site within the tissue 112 using the positioning device 110. For example, the ultrasound source 102 can be positioned such that its focus 120 is a depth within an ex vivo or in vivo organ (e.g., a liver, kidney, heart, and/or other tissue mass) and aligned with a tumor, cancerous tissue region, and/or other volume of tissue that a clinician would like to mechanically damage. HIFU energy can be delivered from the ultrasound source 102 to the target site in the tissue 112 in a sequence of pulses (e.g., coordinated by the function generator 104 and/or the controller 108) rather than continuous-wave HIFU exposures, which can reduce undesirable thermal effects on the surrounding tissue. Larger target sites can be treated by scanning the focus 120 of the ultrasound source 102 over the treatment region (e.g., using the positioning device 110) while pulsing HIFU energy toward the tissue 112.

In various embodiments, the HIFU system 100 can deliver a pulsing protocol to provide boiling histotripsy that mechanically fractionates the tissue. During boiling histotripsy, the ultrasound source 102 propagates millisecond-long bursts of non-linear HIFU waves toward the focal region 120 in the tissue 112, and the accumulation of the harmonic frequencies produces shock fronts proximate to the focal region 120. This results in rapid heating of tissue and boiling bubbles at the focal region 120 that liquefy and otherwise mechanically damages the tissue. In certain embodiments, the function generator 104 can initiate a pulsing protocol to generate shock waves with peak amplitudes of approximately 30-150 MPa at the focus 120. For example, the shock wave amplitudes may be 35 MPa, 40 MPa, 45 MPa, 50 MPa, 55 MPa, 60 MPa, 65 MPa, 70 MPa, 75 MPa, 80 MPa, 85 MPa, 90 MPa, 95 MPa, 100 MPa, 105 MPa, 110 MPa, 115 MPa, 120 MPa, 125 MPa, 130, MPa, 135 MPa, 140 MPa, 145 MPa, 150 MPa, and/or values therebetween. In other embodiments, the shock wave amplitudes may differ depending, at least in part, on the power driving the ultrasound source 102.

Figure 2A:
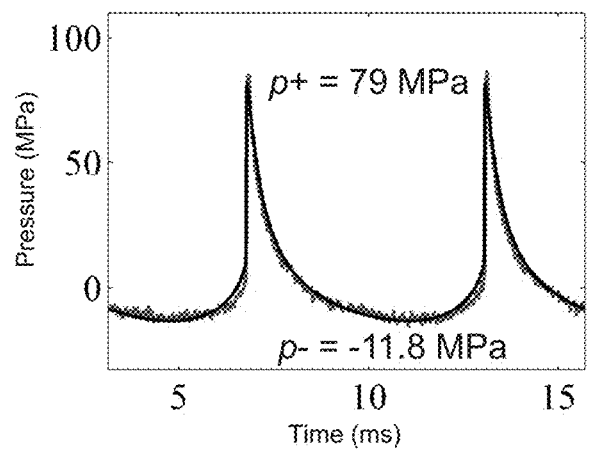
FIGS. 2A and 2B are graphs illustrating focal pressure waveforms produced using HIFU systems configured in accordance with embodiments of the present technology.
Figure 2B:
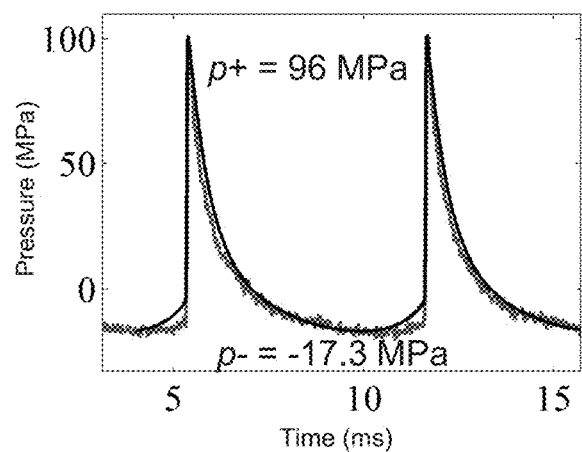

FIGS. 2A and 2B, for example, are graphs illustrating focal pressure waveforms produced using the HIFU system 100 of FIG. 1. In FIG. 2A, the ultrasound source has a power of 250 W and, as shown in the graph, produces HIFU waves having a peak positive pressure of about 79 MPa, a peak negative pressure of about −11.8 MPa, and a shock amplitude of about 80 MPa. In FIG. 2B, the ultrasound source has a power of 600 W and, as shown in the graph, produces HIFU waves having a peak positive pressure of 96 MPa, a peak negative pressure of about −17.3 MPa, and a shock amplitude of about 110 MPa. In other embodiments, the peak positive pressure, the peak negative pressure, and/or the shock amplitude of the HIFU waves may differ depending upon the power of the ultrasound source, the frequency of the ultrasound source, and/or the parameters of the pulsing protocol effectuated by the function generator 104 (FIG. 1). For example, the peak positive pressure can be about 30-125 MPa (e.g., 40 MPa, 50 MPa, 60 MPa, 70 MPa, 80 MPa, 90 MPa, and/or pressure values therein), and the peak negative pressure may be about −30 MPa to −3 MPa (e.g., −20 MPa, −15 MPa, −10 MPa, −5 MPa, and/or pressure values therein). The ultrasound source can have power levels between about 100 W to 5 kW (e.g., 200 W, 300 W, 400 W, 500 W, 600 W, 700 W, 800 W, 900 W, 1 kW, 2 kW, 3 kW, 4 kW, 5 kW, and/or power values therein), or higher.

Referring back to FIG. 1, absorption of ultrasonic energy occurs primarily at the shock front (i.e., at the shock amplitude shown in FIGS. 2A and 2B), and induces rapid heating of the tissue 112 that can boil the tissue 112 within milliseconds. Depending upon the power driving the HIFU system 100 and the acoustic parameters of the tissue 112, the time-to-boil is generally less than 100 ms (e.g., 0.1 ms, 0.5 ms, 1 ms, 5 ms, 10 ms, 15 ms, 30 ms, 40 ms, 50 ms, etc.). For example, the HIFU system 100 can be configured such that the duration of each pulse is at least equivalent to the time necessary to induce tissue boiling at approximately 100° C. Therefore, during each pulse, one or more boiling bubbles can be formed in the tissue 112. In several embodiments, the boiling bubbles can have cross-sectional dimensions of approximately 2-4 mm. In other embodiments, however, the boiling bubbles can be larger or smaller. For example, the boiling bubbles in the tissue 108 can have a cross-sectional dimension between approximately 100 μm and approximately 4 mm (e.g., 0.2 mm, 0.5 mm, 1 mm, 2 mm, 3 mm, etc.) on the order of the beam-width of the ultrasound source 102 at the focus 120. The superheated vapor of the boiling bubbles provides a force pushing outward from the bubble. This repetitive explosive boiling activity and interaction of the ultrasound shock waves with the boiling bubbles emulsifies the tissue 112 at the target site to form a liquid-filled lesion largely devoid of cellular structure, with little to no thermal coagulation within the treated region. For example, in certain embodiments, the HIFU system 100 can deliver a pulsing protocol in which each pulse has a length of 1-15 ms (e.g., 1 ms, 5 ms, 10 ms, etc.), and at least 5 pulses of HIFU energy are delivered at each treatment site at a frequency of 1-10 Hz (1-10% duty cycle) to adequately destroy the desired cellular tissue at the focal region 120. In other embodiments, the number of pulses and the pulse length may differ based on the operating parameters of the ultrasound source 102, the tissue properties, and/or the desired properties of the lesion. For example, the number of pulses per treatment site can range from 1 pulse to more than 100 pulses (e.g., 2 pulses, 5 pulses, 15 pulses, 40 pulses, etc.), the pulse length can be 0.1-100 ms (e.g., 2 ms, 5 ms, 10 ms, 30 ms, 50 ms, etc.), and the frequency or duty cycle of ultrasound application can be 1-20% (e.g., 2%, 3%, 4%, 5%, 6%, 10%, etc.).

In selected embodiments, the pulsing protocol of the HIFU system 100 can be adjusted to minimize the deposition of the HIFU energy in the tissue 112, and thereby reduce the thermal effects (e.g., thermal coagulation, necrotized tissue) of the HIFU treatment. For example, repeating shock waves at a pulse repetition frequency that is slow enough (e.g., approximately 1 Hz or 1% duty cycle) to allow cooling between the pulses such that lesion content within the target site and the surrounding tissue shows minimal to no evidence of thermal denature. In certain embodiments, a duty cycle of less than 10% also allows cooling between pulses that reduces thermal denature. For example, the pulsing protocol can have a duty cycle of 5% of less (e.g., 4%, 2%, 1%, etc.).

In other embodiments, the HIFU system 100 can implement a pulsing protocol that provides cavitation-based histotripsy to mechanically fractionate the tissue 112 at the focus 120. During cavitation histotripsy, the ultrasound source 102 operates at a relatively low duty cycle (e.g., 1%, 2%, 3%, etc.) to emit microsecond-long pulses of HIFU energy (e.g., 10-20 μs) with high pulse average intensities of 50 W/cm$^2$ to 40 kW/cm$^2$ that form cavitation bubbles that mechanically disrupt tissue. In this embodiment, the pulses of HIFU waves generated by the HIFU source 102 have high peak negative pressures, rather than high peak positive pressures used for boiling histotripsy. The peak negative pressure are significantly higher than the tensile strength of the tissue 112 so as to induce cavitation in the tissue 112. For example, the pulsing protocol for cavitation histotripsy can include pulse lengths of 1 μs or longer (e.g., 2-50 μs) and peak negative pressures of about −15 MPa or lower (e.g., −20 MPa, −30 MPa, −50 MPa, etc.). The repetition of such pulses can increase the area of tissue affected by cavitation to create a "cavitation cloud" that emulsifies the tissue.

The degree of mechanical tissue damage induced by histotripsy—boiling or cavitation—depends at least in part on the composition of the tissue. In general, more fibrous structures, such as vasculature and stromal tissue, are more resistant to the HIFU-induced mechanical tissue disruption, whereas cells are more easily lysed. As a result, vessels, ducts, collagenous structures, and other portions of the ECM of the tissue 108 within and surrounding a treatment volume remain at least substantially intact after lesion formation. In addition, the HIFU therapy provided by the HIFU system 100 can be configured to limit the degree of thermal effect on the ECM. For example, the HIFU therapy can be controlled to reduce or minimize the degree of protein denature of the tissue (e.g, less than 20%, 10%, 5%, 4%, 3%, etc.) during lesion formation. Accordingly, histotripsy can be used to decellularize large tissue volumes while sparing the integrity of the ECM.

Figure 3A:
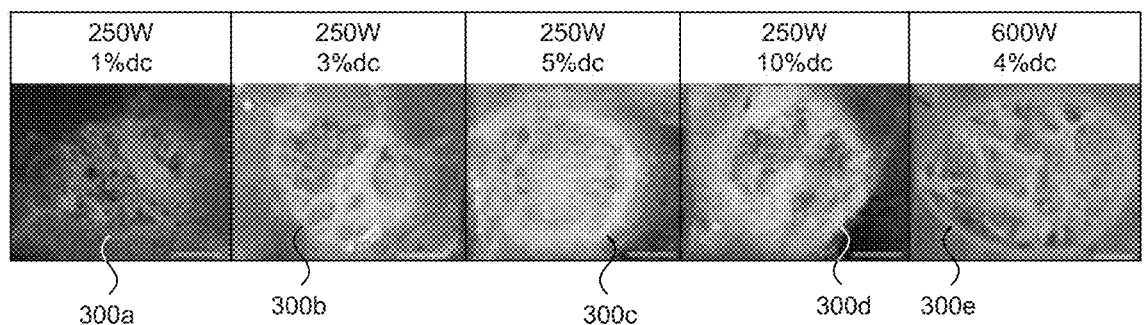
FIG. 3A is a series of images of lesions formed in tissue using HIFU methods in which duty cycle and power were varied in accordance with the present technology.

FIG. 3A, for example, illustrates a series of images of rinsed lesions 300 (identified individually as first through fifth lesions 300a-b, respectively) formed in tissue using boiling histotripsy techniques in which the duty cycle and ultrasound source power were varied in accordance with the present technology. The lesions 300 can be formed using the HIFU system 100 of FIG. 1 and/or other suitable HIFU systems. As shown in FIG. 3A, the first through fourth lesions 300a-300d were formed with an ultrasound source (e.g., the ultrasound source 102 of FIG. 1) set to a power of 250 W with duty cycles ranging from 1% to 10%. The pulsing protocol for first through fourth lesions 300a-d had a pulse length of 10 ms, a pulse repetition of 30 pulses per treatment site, a peak positive pressure of 78 MPa, a shock amplitude of 80 MPa, and a peak negative pressure of −12 MPa. The fifth lesion 300e was formed with an ultrasound source (e.g., the ultrasound source 102 of FIG. 1) set to a power of 600 W and driven by a pulsing protocol having a 4% duty cycle, 1 ms-long pulses, 30 pulses per treatment site, a peak positive pressure of 100 MPa, a shock amplitude of 110 MPa, and a peak negative pressure of −17 MPa. In other embodiments, lesions can be formed using ultrasound sources having higher or lower power values and/or using different pulsing protocol parameters.

In FIG. 3A, the ECM (e.g., vessels and connective tissue) is indicated by the light-colored structures extending through the lesions 300. In each of the five lesions 300, at least a portion of the ECM is not liquefied by the HIFU therapy. However, the images indicate that that smaller vessels and connective tissue of the ECM were less affected by the HIFU therapy when the duty cycle was lower. For example, referring to the lesions 300 formed by the 250 W ultrasound source (lesions 300a-d), the integrity of the vessels and other connective tissue of the ECM are more clearly seen and preserved in the first and second lesions 300a and 300b with duty cycles of 1% and 3%, respectively, than in the third and fourth lesions 300c and 300d with duty cycles of 5% and 10%, respectively, which illustrate structural damage to vasculature and connective tissue. The fifth lesion 300d, which was created using the 600 W ultrasound source and a pulsing protocol having 4% duty cycle has a clearly defined lesion of liquefied tissue, while still at least substantially preserving the structural integrity of the ECM. For example, small caliber blood vessels (e.g., vessels having diameters of less than 50 µm) remained intact in the fifth lesion 300e. Accordingly, it is expected that pulsing protocols with lower duty cycles, shorter pulse lengths, and higher peak positive pressures will facilitate the preservation of the ECM during boiling histotripsy.

Figure 3B:
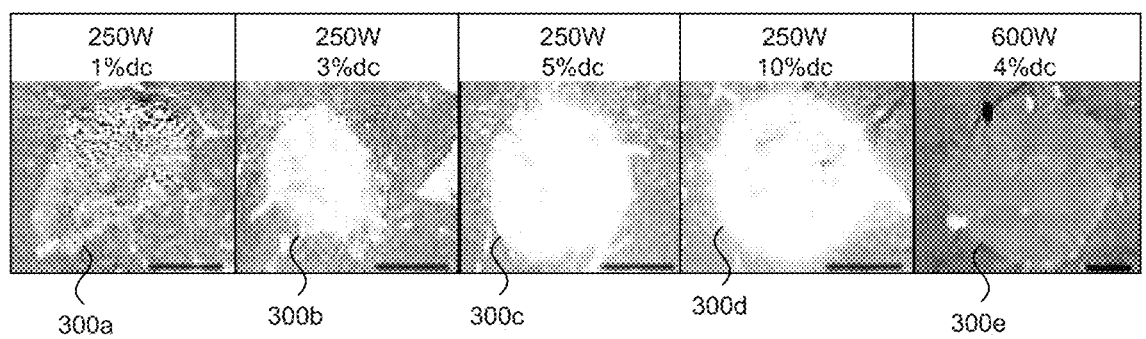
FIG. 3B is a series of histomicrographs of sections of the tissue lesions of FIG. 3A stained with NADH-d.

FIG. 3B is a series of histomicrographs of sections of the tissue lesions 300 of FIG. 3A stained with NADH-d. The NADH-d staining illustrates the degree of thermal damage incurred by the tissue during the boiling histotripsy treatments, with lighter sections (e.g., white) being indicative of thermal damage. Accordingly, FIG. 3B shows that the tissue of the first lesion 300a created using a 250 W source and a 1% duty cycle incurred some thermal damage, but much less thermal damage than the second through fourth lesions 300b-300d, which incurred increasingly more thermal damage as the duty cycle increased. As further shown in FIG. 3B, the tissue of the fifth lesion 300e created using the 600 W ultrasound source incurred very little to no thermal damage from the HIFU therapy. Therefore, FIG. 3B further shows that a higher power source (that emits higher peak positive pressure) operated at a relatively low duty cycle (i.e., 4 Hz) with short pulse lengths (1 ms) incurred the lowest degree of thermal damage. It is expected that decreasing the degree of thermal damage indicates that the ECM has not been damaged by the HIFU therapy. Accordingly, it is further expected that pulsing protocols having low duty cycles (e.g., less than 5%, 4%, 3%, 2%, 1%, etc.), short pulse lengths (e.g., 1 ms, 2 ms, 3 ms, 5 ms, 10 ms, etc.), and higher peak positive pressures (e.g., 70 MPa, 80 MPa, 90 MPa, 100 MPa, 125 MPa, etc.) will create lesions with limited thermal damage and increased overall preservation of the ECM within the treatment volume. The parameters of the pulsing protocol can accordingly be selected based on acceptable levels of ECM degradation and thermal damage.

Referring back to FIG. 1, the HIFU systems 100 can be used to selectively disrupt tissue to lyse cells, while limiting damage to the ECM within a treated tissue volume. Therefore, HIFU therapy can be used to treat volumes of tissue that include vasculature and/or other portions of an ECM that may wish to be preserved after HIFU therapy. For example, HIFU therapy can be used in vivo to emulsify malignant or benign tumors in a volume of tissue (e.g., the prostate, kidneys, liver, and/or other body parts) that includes vessels or other structural features. This is expected to allow clinicians to treat larger tissue volumes using HIFU therapy with less concern for the vessels or other desired ECM structures may lie therein because the ECM remains at least substantially intact even though it is exposed to the focus of the HIFU therapy beam. For example, HIFU therapy can be used to create single lesions of 1-4 cm$^3$ or larger (e.g., 5 cm$^3$, 6 cm$^3$ 7 cm$^3$, etc.).

Depending on the composition of the treated tissue, the ECM remaining in the lesion after HIFU therapy can include a fibrous, vascularized structure that can serve as a scaffold on which cells can grow. For example, when the HIFU is used to form a lesion in vivo, the HIFU therapy can at least substantially decellularize the treatment volume, leaving only the ECM scaffolding. The body may naturally repopulate the ECM scaffolding with healthy cells to regrow tissue in the region where the diseased cells were previously lysed by the HIFU therapy. In certain embodiments, the tissue re-growth can be supplemented by disposing or injecting cells (e.g., stem cells or cells of the same type of tissue) with or without a carrier or other delivery mechanism (e.g., a gel) on the ECM scaffold to stimulate cell regrowth and regenerate the previously-destroyed tissue mass.

In various embodiments, HIFU therapy can be used to at least partially decellularize entire organs or other tissue masses that include an ECM to create a scaffold or structure for regenerative medicine. Because the ECM naturally serves as the structural framework for tissue systems, the use of histotripsy to strip away cells results in a naturally-derived, pre-vascularized three-dimensional support structure for cell regrowth. For example, the HIFU system 100 of FIG. 1 can apply HIFU therapy across an organ ex vivo organ. The function generator 104 and/or the controller 108 can implement a pulsing protocol via the HIFU source 102 to decellularize tissue at the focal region 120, and the focal region 120 can be moved or scanned across different portions of the organ (e.g., using the positioning device 110) while the pulsing protocol is implemented to at least substantially decellularize the organ. As discussed above, the ECM of the treated tissue mass will remain at least substantially intact, and therefore the decellularized tissue can serve as a decellularized scaffold that includes the same vasculature, stromal tissue, and/or other structures of the ECM as the organ would in vivo. Unlike the biomimetic scaffolds that are artificially created to mimic the vasculature and structure of an organ or tissue mass and difficult to form due to the complexities mimicking the ECM, the decellularized scaffolds formed using the HIFU methods disclosed herein are pre-vascularized and inherently include the necessary structure for cell growth. Thus, using HIFU methods to form decellularized scaffolds is expected to facilitate the formation of decellularized scaffolds and enhance the ease of cell incorporation because the scaffolds are inherently more similar to natural body structures than artificial scaffolds. In addition, these large structures (e.g., entire organs) can easily be perfused to support the tissue engineered organ as it forms and grows, and can be connected to the native vasculature of the patient upon implantation.

In various embodiments, organs or tissue masses can be regenerated by disposing stem cells and/or other cells on the decellularized scaffold (i.e., as defined by the ECM structure) to regrow or regenerate the organ or tissue ex vivo. The regenerated organ or tissue mass can then be implanted into the body of a human patient during a transplant procedure. In other embodiments, the decellularized scaffold can be implanted in the body, and the body itself can form cells on the scaffold to regenerate the tissue mass or organ. In certain embodiments, the growth of cells on the implanted scaffold can be facilitated by disposing or injecting cells (e.g., stem cells) on the implanted scaffold. Due to the bare (i.e., cell-free or substantially cell-free) composition of the decellularized scaffold, the decellularized scaffold (as defined by the ECM) is expected to induce a relatively weak immune response of the host when implanted in the body.

Current methods of decellularizing ex vivo organs and other tissue masses require perfusing the organ or tissue with a chemical and/or enzymatic detergent through the organ. Perfusion decellularization, as it is known in the art, generally requires that the organ or tissue be perfused for multiple days, if not more, and can result in alterations or damage to tissues and fibers due, at least in part, to the extended exposure to the chemicals and enzymes. In contrast, the disclosed histotripsy methods can decellularize a tissue mass or an entire organ in significantly less time. For example, the lesions shown in FIGS. 3A and 3B were formed within 20 minutes. In practice, an organ that may take several days to decellularize via perfusion may only take hours to decellularize via histotripsy. In certain embodiments, multiple ultrasound sources 102 can projected toward different portions of the organ or tissue mass at the same time to decrease the total decellularization time. Accordingly, it is believed that HIFU decellularization of a tissue mass using the techniques described herein is substantially faster (e.g., about 40 times faster) than with perfusion decellularization.

In various embodiments, HIFU decellularization can be used in conjunction with or to supplement perfusion decellularization. For example, a tissue mass can undergo HIFU treatment to crudely decellularize the tissue, and then the tissue mass can be perfused using chemical or enzymatic agents to remove any remaining cells. In other embodiments, perfusion decellularization and HIFU decellularization can occur simultaneously to expedite the decellularization process. In any of these combined decellularization methods, the total time to decellularize a tissue mass is substantially reduced from the time it would take to decellularize the tissue mass using perfusion alone.

Figure 4:
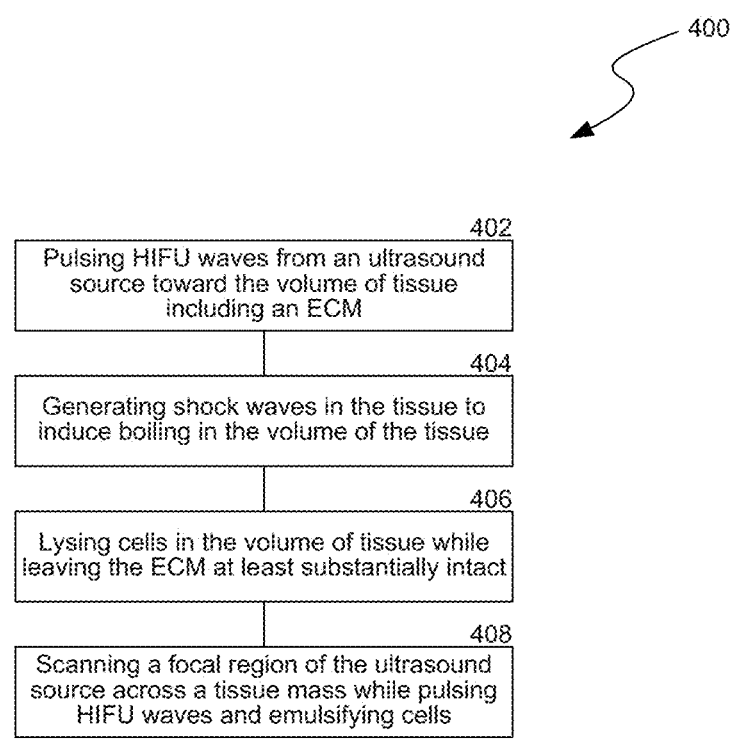
FIG. 4 is a block diagram illustrating a method of treating tissue at a target site configured in accordance with an embodiment of the present technology.

FIG. 4 is a block diagram illustrating a method 400 configured in accordance with an embodiment of the present technology. The method 400 can be implemented with the HIFU system 100 of FIG. 1 and/or other suitable HIFU systems. The method 400 includes positioning a focus of an ultrasound source in a tissue volume including an ECM, and pulsing HIFU waves from the ultrasound source toward the volume of tissue (block 402). The ECM of the tissue volume depends on the type of tissue or organ being treated, and may include vasculature, stromal tissue, collecting ducts, tubules, glomeruli, portal structures, and/or other fibrous, non-cellular structures. As discussed above, the focus of the ultrasound source can be mechanically or manually aligned with the target site in the tissue. The pulsed HIFU waves can be provided in accordance with a predefined pulsing protocol for boiling histotripsy and/or cavitation histotripsy that induces the selective mechanical disruption of tissue. As discussed above, pulsing protocols can include a variety of different factors that can induce millisecond boiling with little to no thermal denature around and in the lesion. For example, a pulsing protocol can take into account the frequency at an ultrasound source, the power of the ultrasound source, peak positive pressure at the focus of the ultrasound source, peak negative pressure at the focus, shock amplitude, pulse length, pulse repetition frequency, and duty cycle. In certain embodiments, for example, the pulsing protocol can have a peak positive pressure of 30-125 MPa (e.g., 40 MPa, 50 MPa, 60 MPa, 70 MPa, 75 MPa, 80 MPa, 90 MPa, etc.), a pulse length of 100 ms or less (e.g., 1 µm, 0.1 ms, 1 ms, 10 ms, 20 ms, etc.), and a duty cycle of 5% or less (e.g., 4%, 3%, 2%, 1%, etc.). In other embodiments, the values of the pulsing protocol parameters can differ and/or the pulsing protocol can include additional factors related to tissue fragmentation using histotripsy.

As the HIFU waves are pulsed into the tissue, the HIFU energy can generate shock waves in the tissue proximate to the focus of the ultrasound source to induce boiling in the volume of tissue (block 404). The energy from the shock waves can cause boiling bubbles in the tissue within milliseconds. By way of specific examples, shock waves with amplitudes of about 70-80 MPa delivered by an ultrasound source with a power of 250 W can induce boiling bubbles within 10 ms, and shock waves with amplitudes of about 100-110 MPa delivered by an ultrasound source with a power of 600 W can induce boiling bubbles within 1 ms. This rapid millisecond boiling followed by the interaction of shock fronts from the rest of the pulse with the boiling vapor cavity lyses cells without affecting more fibrous structures of the ECM. Accordingly, the method 400 continues by lysing cells in the volume of tissue, while leaving the ECM at least substantially intact (block 406). In various embodiments, the duty cycle, the pulse length, and/or other parameters of the pulsing protocol can be selected to reduce or minimize the degree of damage to the ECM and/or thermal damage to the tissue in and surrounding the lesion. For example, the pulsing protocol can have a duty cycle of 5% or less (e.g., 4%, 3%, 2%, 1%, etc.) and a pulse length of 10 ms or less (e.g., 9 ms, 8 ms, 7 ms, 6 ms, 5 ms, 4 ms, 3 ms, 2 ms, 1 ms, etc.). Because the HIFU method 400 preserves the ECM, the method 400 can be used to treat larger tissue volumes and masses, without concern for the ECM that lies therein. For example, the method 400 can be used to treat a volume of tissue in the liver without destroying the portal structures and vasculature therein.

The method 400 can optionally include scanning a focal region or focus of the ultrasound source across a tissue mass while pulsing HIFU waves and lysing cells (block 408). When the treatment site is larger than the focal region of the ultrasound source, the focus of the ultrasound source can be mechanically or manually moved to an adjacent tissue region where the pulsing protocol can again be implemented to lyse cells while at least substantially preserving ECM of the treated tissue region. Accordingly, the method 400 can be used to decellularize large tissue masses in vivo or ex vivo. The bare ECM remaining after HIFU therapy can provide a naturally-derived pre-vascularized three-dimensional scaffold that can be used to regrow tissue. For example, if decellularized outside of the body, the scaffold can be implanted in the body and injected with cells (e.g., stem cells) to regenerate the tissue or organ. In certain embodiments, the cells may be in or on a carrier (e.g., a gel) and the carrier can be disposed on the decellularized scaffold. Alternatively, the decellularized scaffold can be injected with cells ex vivo to regenerate the tissue or organ, and then can be implanted. In other embodiments, the tissue mass is decellularized in vivo, and healthy tissue can regenerate on the decellularized scaffold (e.g., with or without additional cell injection).

Figure 5:
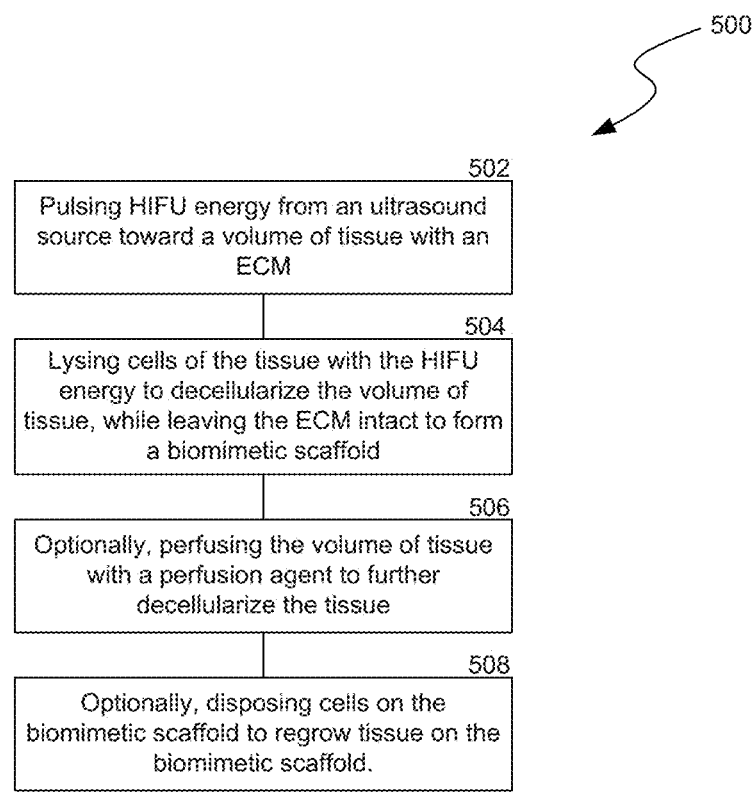
FIG. 5 is a block diagram illustrating a method of forming decellularized scaffolds configured in accordance with an embodiment of the present technology.

FIG. 5 is a block diagram illustrating a method 500 of forming a decellularized scaffold configured in accordance with an embodiment of the present technology. The method 500 can be implemented with the HIFU system 100 of FIG. 1 and/or other suitable HIFU systems and can be performed on a tissue mass in vivo or ex vivo. As shown in FIG. 5, the method 500 can include pulsing HIFU energy from an ultrasound source toward a volume of tissue including an ECM (block 502). The HIFU energy can be pulsed in accordance with the pulsing protocols described above to mechanically disrupt the tissue using either boiling histotripsy or cavitation histotripsy techniques. The method 500 continues by lysing cells of the tissue with the HIFU energy to at least substantially decellularize the volume of tissue (block 504). This step leaves the ECM intact such that the ECM can be used to provide a decellularized scaffold that can be used to subsequently regenerate tissue (block 504). The emulsification of most or all cells within the tissue volume can occur within minutes. Accordingly, the ultrasound source can be scanned across a tissue mass or organ to at least substantially decellularize the entire tissue mass or organ within a relatively short period of time (e.g., within several hours). Unlike artificial scaffolds used in regenerative medicine, the biomimetic structures formed using this method 500 provides a naturally-derived pre-vascularized three dimension structure on which new tissue can grow. In addition, the method 500 is expected to take much less time to decellularize the tissue than chemically-induced perfusion decellularization.

As further shown in FIG. 5, the method 500 can optionally include perfusing a volume of the tissue with a perfusion agent (e.g., a chemical and/or enzymatic detergent) to further decellularize the tissue (step 506). The perfusion can occur before, during, and/or after the HIFU decellularization. For example, HIFU can be used to partially decellularize an organ ex vivo and the remaining cells can be removed via perfusion.

Once the ECM is decellularized, the method 500 can continue by disposing cells (e.g., stem cells) on the decellularized scaffold formed by the bare ECM to regrow tissue on the decellularized scaffold (block 508). In certain embodiments, the decellularized scaffold can be formed ex vivo, implanted in the body of a human patient, and then cells can be injected into the decellularized scaffold to regenerate the tissue on the ECM. In other embodiments, the regrowth of the tissue on the decellularized scaffold is performed ex vivo, and the regrown tissue mass (e.g., an organ) can be implanted in the human body. The bare composition of the naturally-derived scaffold is expected to have only a relatively weak immune response from the host when implanted within the body.

EXAMPLES

1. A method of treating tissue, the method comprising:
pulsing high intensity focused ultrasound (HIFU) waves from an ultrasound source toward a volume of tissue that includes an extracellular matrix (ECM);
generating, from nonlinear propagation of the HIFU waves, shock waves in the tissue to induce boiling in the volume of the tissue at a focus of the ultrasound source; and
lysing cells in the volume of tissue, via the HIFU waves, while leaving the ECM at least substantially intact.

2. The method of example 1 wherein the focus of the ultrasound source is positioned a depth within the tissue, and wherein generating shock waves in the tissue includes generating shock waves having a peak positive pressure at the focus of at least 50 MPa.
3. The method of example 1 or example 2 wherein pulsing HIFU waves comprises pulsing HIFU waves such that each pulse has a duration of 0.1-100 ms.
4. The method of any one of examples 1-3 wherein pulsing the HIFU waves further comprises pulsing the HIFU waves at a duty cycle of at most 5%.
5. The method of example 1 wherein:
the ultrasound source has a power of 250-5,000 W;
pulsing the HIFU waves further comprises pulsing the HIFU waves at a duty cycle of at most 5%, wherein individual pulses have a pulse length of 1-10 ms;
generating shock waves further comprises generating shock waves having a peak positive pressure of 50-150 MPa; and
lysing cells in the volume of tissue comprises preserving vessels in the volume of tissue having diameters of less than 50 µm.
6. The method of any one of examples 1-5 wherein lysing cells in the volume of tissue further comprises at least substantially decellularizing the tissue to create a scaffold for subsequent cell regrowth.
7. The method of any one of examples 1-6 wherein the volume of tissue is part of an ex vivo organ, and wherein:
lysing cells in the volume of tissue further comprises at least substantially decellularizing the volume of tissue; and
the method further comprises moving a focus of the ultrasound source across the organ while pulsing HIFU waves and lysing cells to create a decellularized scaffold of the ex vivo organ.
8. The method of example 7, further comprising disposing cells on the decellularized scaffold to re-grow the organ.
9. The method of any one of examples 1-6 wherein the volume of tissue is part of an in vivo tissue mass, and wherein:
lysing cells in the volume of tissue further comprises at least substantially decellularizing the tissue; and
moving a focal region of the ultrasound source across the tissue mass while pulsing HIFU waves and lysing cells to create a decellularized scaffold.
10. The method of any one of examples 1-9 wherein emulsifying the cells in the volume of tissue while leaving the ECM at least substantially intact further comprises forming a lesion in the tissue having a volume of at least 1 cm$^3$.
11. The method of any one of examples 1-10 wherein the shock waves in the tissue are distinct from shock waves resulting from cavitation.
12. A method of treating tissue, the method comprising:
applying, via an ultrasound source, high intensity focused ultrasound (HIFU) energy to a target site in tissue in accordance with a pulsing protocol, wherein
the individual pulses have a length of 0.1-100 ms,
the HIFU energy generates shock waves proximate to the target site in the tissue to induce boiling of the tissue at the target site, and
the target site is proximate to a focal region of the ultrasound source; and
forming a lesion in the tissue with the HIFU energy while preserving an extracellular matrix (ECM) in the lesion.

13. The method of example 12 wherein forming the lesion in the tissue comprises at least decellularizing the tissue such that the ECM within the lesion is at least substantially free of cells.
14. The method of example 12 or example 13 wherein applying HIFU energy to the target site comprises:
pulsing HIFU waves at a duty cycle of at most 5%; and
generating shock waves having a peak positive pressure of 50-150 MPa.
15. A method of forming decellularized scaffolds, the method comprising:
pulsing high intensity focused ultrasound (HIFU) energy from an ultrasound source toward a volume of tissue, wherein the volume of tissue includes an extracellular matrix (ECM); and
lysing cells of the tissue with the HIFU energy to at least partially decellularize the volume of tissue while leaving the ECM at least substantially intact to form a decellularized scaffold for subsequent tissue growth.
16. The method of example 15 wherein pulsing HIFU energy toward the volume of tissue comprises generating, from nonlinear propagation of HIFU waves, shock waves in the tissue to induce boiling in the tissue.
17. The method of example 15 wherein pulsing HIFU energy toward the volume of tissue comprises applying cavitation histotripsy to form a lesion in the volume of tissue.
18. The method of any one of examples 15-17, further comprising moving a focal region of the ultrasound source across portions of the tissue while pulsing the HIFU energy and lysing cells to form a lesion in the tissue having a volume of at least 1 cm$^3$.
19. The method of any one of examples 15-18 wherein the tissue is part of an ex vivo organ of a human body, and wherein emulsifying cells comprises decellularizing the ex vivo organ.
20. The method of example 19, further comprising disposing cells on the decellularized scaffold to re-grow the organ.
21. The method of any one of examples 15-20, further comprising perfusing vessels of the tissue with a decellularization detergent to further decellularize the tissue.
22. The method of example 21 wherein perfusing vessels of the tissue with a decellularization agent occurs while the HIFU energy is applied to the tissue.
23. The method of any one of examples 15-22 wherein the tissue is part of an in vivo organ of a human body, and wherein lysing cells comprises decellularizing at least a portion of the in vivo organ.
24. The method of any one of examples 15-23 wherein pulsing HIFU energy further comprises applying HIFU energy to the volume of tissue in accordance with a pulsing protocol having a duty cycle of less than 5% and a pulse duration of at most 100 ms.
25. A high intensity focused ultrasound (HIFU) system for forming decellularized scaffolds, the HIFU system comprising:
an ultrasound source having a focal region and configured to deliver HIFU waves to a target site in tissue of a subject; and
a controller having a function generator operably coupled to the ultrasound source, wherein—
the controller comprises a non-transitory memory that includes a pulsing protocol for delivering HIFU energy with the ultrasound source, wherein the pulsing protocol has a pulse length of 0.01-100 ms, and a duty cycle of less than 10%,
the controller is configured to cause the ultrasound source to pulse HIFU waves to lyse cells in a volume of the tissue of the subject while preserving an extracellular matrix (ECM) in the volume of the tissue exposed to the HIFU waves, and
the ECM defines a decellularized scaffold.
26. The HIFU system of example 25 wherein the pulsing protocol of the controller has a peak positive pressure of at least 70 MPa.
27. The HIFU system of example 25 or example 26 wherein the pulsing protocol of the controller has a pulse length of at most 10 ms.
28. The HIFU system of any one of examples 25-27 wherein the pulsing protocol of the controller has duty cycle of at most 4%.
29. The HIFU system of example 25 wherein the HIFU energy generates shock waves at the focal region in the tissue to induce boiling in the tissue.
30. The HIFU system of example 25 wherein the HIFU energy generates cavitation bubbles in the tissue at the focal region.
31. The HIFU system of example 25 wherein the pulsing protocol of the controller has a peak negative pressure at the focal region of −15 MPa or less.

CONCLUSION

From the foregoing, it will be appreciated that specific embodiments of the technology have been described herein for purposes of illustration, but that various modifications may be made without deviating from the disclosure. For example, the HIFU system 100 of FIG. 1 can include additional devices and/or systems to facilitate selectively fragmenting tissue volumes. For example, the HIFU system 100 can include additional amplifiers, high-pass or other suitable filters, perfusion decellularization systems, and/or other suitable devices related to HIFU and decellularization of tissue masses. Certain aspects of the new technology described in the context of particular embodiments may be combined or eliminated in other embodiments. Additionally, while advantages associated with certain embodiments of the new technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein. Thus, the disclosure is not limited except as by the appended claims.

We claim:
1. A system comprising:
an ultrasound source having a focal region and configured to deliver high intensity focused ultrasound to a target site in a tissue; and
a controller operably coupled to the ultrasound source, wherein the controller causes the ultrasound source to deliver the high intensity focused ultrasound in pulses having a pulse length in a range of about 1 millisecond (ms) to about 10 ms and a duty cycle in a range of about 1% to about 5%, thereby lysing cells in the target site and substantially preserving an extracellular matrix in the target site,
wherein vessels in the tissue are perfused with a decellularization detergent when the high intensity focused ultrasound is delivered to the target site in the tissue.

2. The system of claim 1 wherein the high intensity focused ultrasound generates shock waves at the focal region to induce boiling in the tissue.

3. The system of claim 1 wherein the high intensity focused ultrasound generates cavitation bubbles in the target site.

4. The system of claim 3 wherein the high intensity focused ultrasound generates shock waves at the focal region to induce boiling in the tissue, and
wherein the shock waves are distinct from shock waves resulting from cavitation.

5. The system of claim 1 wherein the pulses have a peak positive pressure of at least 50 MPa.

6. The system of claim 1 wherein the duty cycle is less than or equal to 4%.

7. The system of claim 1 wherein a peak negative pressure of the pulses at the focal region is less than or equal to −15 MPa.

8. A method, comprising:
lysing cells in a target site and substantially preserving an extracellular matrix at the target site by transmitting, by an ultrasound source, pulses of high intensity focused ultrasound having a pulse length in a range of about 1 millisecond (ms) to about 10 ms and a duty cycle in a range of about 1% to about 5%, a focal region of the high intensity focused ultrasound overlapping the target site; and
simultaneously with transmitting the pulses of the high intensity focused ultrasound, perfusing, with a decellularization detergent, vessels of a tissue comprising the target site.

9. The method of claim 8 wherein transmitting the pulses of the high intensity focused ultrasound comprises generating, from a nonlinear propagation of the high intensity focused ultrasound, shock waves in the target site to induce boiling in the target site.

10. The method of claim 8 wherein transmitting the pulses of high intensity focused ultrasound comprises generating a lesion in the target site by applying cavitation histotripsy to the target site.

11. The method of claim 8, the target site being a first target site in a tissue, the method further comprising:
moving the focal region to a second target site; and
lysing cells in the second target site and preserving an extracellular matrix in the second target site by transmitting, by the ultrasound source, second pulses of the high intensity focused ultrasound,
wherein lysing the cells in the first target site and lysing the cells in the second target site generates a lesion in the tissue having a volume of at least 1 cm$^3$.

12. The method of claim 8 wherein the target site is part of an ex vivo or in vivo organ of a human body, and wherein lysing the cells in the target site and preserving the extracellular matrix in the target site comprises decellularizing the part of the ex vivo or in vivo organ.

13. The method of claim 12, further comprising disposing cells on a decellularized scaffold comprising the extracellular matrix to re-grow the part of the ex vivo or in vivo organ.

14. The method of claim 11, wherein lysing the cells in the first target site and lysing the cells in the second target site decellurizes the lesion in less than one day.

15. A system for lysing cells in a tissue and preserving an extracellular matrix (ECM) of the tissue, the system comprising:
an ultrasound source configured to transmit high intensity focused ultrasound (HIFU) simultaneously with vessels in the tissue being perfused with a decellularization agent, a focal region of the HIFU being located in the tissue; and
a controller operatively coupled to the ultrasound source and configured to cause the ultrasound source to transmit the HIFU in pulses having a duty cycle of about 1% to about 5%.

16. The system of claim 15, wherein the pulses generate a peak positive pressure of about 70 megapascals (MPa) to about 125 MPa.

17. The system of claim 15, wherein the pulse have a pulse length of about 1 ms, and wherein the duty cycle is about 4%.

18. The system of claim 15, wherein the ultrasound source comprises a 250 W source or a 600 W source.

* * * * *